United States Patent [19]

Beachell

[11] Patent Number: 4,840,788

[45] Date of Patent: Jun. 20, 1989

[54] NONALCOHOLIC SUNSCREEN GEL

[75] Inventor: Vicki T. Beachell, Claymont, Del.

[73] Assignee: ICI Americas Inc., Wilmington, Del.

[21] Appl. No.: 219,589

[22] Filed: Jul. 15, 1986

[51] Int. Cl.$^4$ .......................... A61K 7/40; A61K 7/42; A61K 7/44

[52] U.S. Cl. ....................... 424/59; 424/60; 514/944

[58] Field of Search ............... 424/59, 60; 514/944

[56] References Cited

U.S. PATENT DOCUMENTS

| | | | |
|---|---|---|---|
| 2,561,468 | 7/1951 | Guest | 260/472 |
| 2,614,940 | 10/1952 | Freyermuth et al. | 106/125 |
| 2,876,210 | 3/1959 | Wynn et al. | 260/49.95 |
| 3,065,144 | 11/1962 | Kreps | 424/59 |
| 3,160,665 | 12/1964 | Siegrist et al. | 260/591 |
| 3,270,045 | 8/1966 | Stroebel et al. | 260/465 |
| 3,272,810 | 9/1966 | Stroebel et al. | 260/247.1 |
| 3,341,465 | 9/1967 | Kaufman | 514/873 X |
| 3,403,207 | 9/1968 | Kreps et al. | 424/60 |
| 3,415,875 | 12/1968 | Leuethi et al. | 260/511 |
| 3,506,752 | 4/1970 | Gerecht et al. | 421/60 |
| 3,666,732 | 5/1972 | Skoultchi et al. | 260/78.5 |
| 3,670,074 | 6/1972 | Doner | 424/60 |
| 3,751,563 | 8/1973 | Richardson | 424/60 |
| 3,775,448 | 11/1973 | Guhr | 260/410.7 |
| 3,863,007 | 1/1975 | Warner | 424/60 |
| 3,875,198 | 4/1975 | Stroebel | 260/404 |
| 3,880,992 | 4/1975 | Smolin et al. | 424/60 |
| 4,078,054 | 3/1978 | Isermann et al. | 424/60 |
| 4,132,774 | 1/1979 | Strebel | 424/60 |
| 4,254,102 | 3/1981 | Kaplan et al. | 424/60 |
| 4,256,664 | 3/1981 | Epstein et al. | 564/177 |
| 4,457,911 | 7/1984 | Coner et al. | 424/59 |
| 4,489,057 | 2/1984 | Welters et al. | 424/47 |
| 4,559,225 | 12/1985 | Fourman | 424/59 |
| 4,562,067 | 12/1985 | Hopp et al. | 424/59 |
| 4,584,190 | 12/1986 | Tejima et al. | 424/59 |
| 4,608,392 | 8/1986 | Jacquet et al. | 424/59 |
| 4,654,339 | 3/1987 | Hanefeld et al. | 424/59 |
| 4,671,956 | 6/1987 | Bouillon et al. | 424/59 |
| 4,683,134 | 7/1987 | Palinczar | 424/59 |
| 4,749,563 | 6/1988 | Georgalas | 424/59 |

OTHER PUBLICATIONS

"Clear Gels Formulary", brochure by ICI America, Inc., published 3/72.

Cosmetics and Toiletries, 3/1976, vol. 91, p. 93.

*Primary Examiner*—Dale R. Ore

[57] ABSTRACT

Clear sunscreen gel formulations comprising a water phase and an oil phase are presented which content PABA class UVB type and benzophenone class UVA type absorbing compounds.

6 Claims, No Drawings

NONALCOHOLIC SUNSCREEN GEL

The present invention is directed to blends of ultraviolet absorbing compounds selected from the PABA derivatives with the benzophenone type derivatives which are useful in protecting skin against the harmful effects of actinic radiation. Specifically, it is directed to an oil-in-water emulsion of these UV absorbing compounds in the form of a clear, transparent gel free of ethyl alcohol. They are particularly useful in protecting those who are physiologically affected by the absorption of alcohol into the bloodstream.

Ultraviolet radiation absorbing lotions containing compounds which absorb in the UVB (burning range) such as the PABA derivatives are further improved by the incorporation therewith of UVA (tanning range) absorbing compounds against severe erythremia, edema and blistering when exposed to sunlight. The PABA derivatives and benzophenones of this invention are generally referred to as sunscreen compositions and blends thereof can be incorporated with waxes and oils for the manufacture of cosmetics, lotions, stick formulations, suntan oils, lotions, lipsticks and hair treatments for use by humans and especially those who are sensitive to ethyl alcohol.

Heretofore the formation of clear gels comprising the PABA derivatives and benzophenones UV absorbing compounds in the absence of ethyl alcohol was unknown. Because of their peculiar insolubility, alcohol had to be combined with the ingredients to produce clear gels and solutions. It has now been found that a clear, elegant, oil-in-water transparent gel can be formulated in the absence of ethyl alcohol, utilizing specific combinations of mineral oil, emulsifiers, propylene glycol, sorbitol and water.

The UV absorbing compounds considered as PABA derivatives include alkyl esters of monohydric alcohols having 5–10 carbon atoms of p-dialkylaminobenzoic acid. Especially useful are p-dimethylaminobenzoic acid esters of butyl, amyl, isoamyl and 2-ethylhexyl (octyl) alcohols. Such compounds include esters of unsaturated monohydric alcohols, hydroxyalkyl substituted p-aminobenzoic acid esters, monoalkylaminobenzoic esters, 2,2-dialkylaminoalkanols or alkanol amines, benzoic acid esters and amides, dialkyl quaternary ammonium salts of dialkylaminoalkyl p-dialkylaminobenzoate.

The benzophenone sunscreens are the series benzophenone-1 through benzophenone-12 are represented by the following general structure:

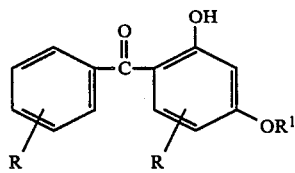

wherein one R is hydrogen and the other R is an alkaline sulphonate radical and $R^1$ is —H or —$CH_3$. The sulphonic acid is neutralized with any various alkaline materials including alkaline earth metals, ammonia, amines such as aliphatic, aromatic, cycloparaffinic and heterocyclic amines and preferably alkali metals, alkali hydroxides, or alkaline alkali metal salts such as sodium carbonate. In some derivatives, at least one of the hydroxyl hydrogens is replaced by a methyl or ethyl group. One such compound, 2-hydroxy-4-methoxy-benzophenone-5-sulfonic acid, is available commercially under the trademark "UVINUL MS-40" and is referred to generically as benzophenone-4. 2,2-dihydroxy-4-methoxybenzophenone is referred to as benzophenone-8. Additional benzophenone type benzophenone UV absorbents include 2,2'-dihydroxy-4,4'-di-substituted benzophenones wherein the 4,4' positions are either hydroxy or alkoxy substituents. Benzophenone-3 2-hydroxy-4-methoxybenzophenone is a preferred UV absorbent and is supplied under the trademark ARLATONE® UVA.

The UVB/UVA weight ratio in sunscreening agents can be varied to produce combinations having skin protection factors (SPF) values ranging from 5–20 when used in weight ratios of from 3/1 at concentrations ranging from 5–30% in the formulation. For example, a weight ratio of 3/1 is employed with isoamyl-p-dimethylaminobenzoate and benzophenone-3 at concentrations of 10% provides a clear sunscreen gel with an SPF of 15.

The gels of the invention comprise an oil phase which consists of mineral oil, vegetable oil, or in some instances, clear silicone oil. Thick and rigid, clear glass-like formulations are formed by the inclusion of pure petroleum wax.

In general, the clear gel is formed by first melting together the PABA and the benzophenone compounds. This is then dissolved in the oil or liquid wax along with appropriate emulsifying agents having an HLB in the range of 1–19 and preferably in the range of 10–15. Such preferred oil-in-water emulsifiers consist of polyethoxylated saturated or unsaturated alcohols having 14–20-carbon atoms and from 2–25 mols of ethylene oxide per molecule such as 2-dendro oleyl alcohol and 20-dendro isohexadecyl alcohol and the like. Numerous other surfactants and blends are commercially available having an appropriate HLB for this use.

The liquid oil phase is mixed with an aqueous phase which contains emollients such as propylene glycol, ethylene glycol and sorbitol, coloring agents, perfumes, stabilizers, anti-oxidants and in some instances medicaments, provided that such combinations produce a clear aqueous solution. The oil phase and water phases are then combined, usually hot, with mild agitation sufficient to disperse the oils in water to form a homogenous clear gel when cooled. By clear gel it is meant that the final cooled product in thicknesses of one centimeter is clear enough to transmit an undistorted image when viewed from one side. The oil phase may comprise from 35–55 percent fo the total formulation.

For topical application, sunscreen compositions made according to the formulations of the invention are non-irritating to the skin tissue and capable of application to the skin in a uniform, continuous film. They are chemically stable and resistant to photodegradation and perspiration and may be absorbed through the skin without physiological contra-indications. Such elegant gels can be applied to form a non-sticky film which may be removed when desired by application of soap and water.

The invention is better understood with reference to the following non-limiting examples wherein all proportions are parts by weight and CTFA name is the generic description provided by the Cosmetic Ingredient Dictionary:

EXAMPLE 1

Clear Sunscreen Gel

| PHASE | INGREDIENTS/ TRADEMARK | CTFA NAME | PERCENT (W/W) |
|---|---|---|---|
| A | ARLATONE® UVB | Octyl Dimethyl PABA | 7.00 |
|   | ARLATONE® UVA | Benzophenone-3 | 3.00 |
| B | Mineral Oil, Light | Mineral Oil | 10.00 |
| C | BRIJ® 93 | Oleth-2 | 6.25 |
|   | ARLASOLVE® 200 | Isoceteth-20 | 18.75 |
| D | Water | Water | 43.00 |
|   | Propylene Glycol | Propylene Glycol | 5.00 |
|   | SORBO® | Sorbitol | 7.00 |

Preparation

In Phase A, add ARLATONE® UVA to ARLATONE® UVB and heat, while mixing, to 50° C. or until the solution becomes clear. In Phase C, add BRIJ® 93 to ARLASOLVE® 200 heat, while mixing, to 50° C. or until the solution becomes clear. Add Phase A to Phase C while mixing. Add Phase B to Phase C while mixing. Heat Phase A/B/C to 80° C. while mixing. Mix Phase D and heat to 85° C. Add Phase D to Phase A/B/C with moderate agitation. Cool to 75° C. and replace water lost by evaporation while mixing, Cool to 70° C. and package.

EXAMPLE 2

Clear Sunscreen Gel

| PHASE | INGREDIENTS/ TRADEMARK | CTFA NAME | PERCENT (W/W) |
|---|---|---|---|
| A | ARLATONE® UVB | Octyl Dimethyl PABA | 7.00 |
|   | ARLATONE® UVA | Benzophenone-3 | 3.00 |
| B | Mineral Oil, Light | Mineral Oil | 10.00 |
| C | BRIJ® 93 | Oleth-2 | 6.25 |
|   | ARLASOLVE® 200 | Isoceteth-20 | 18.75 |
| D | Water | Water | 40.00 |
|   | Propylene Glycol | Propylene Glycol | 4.00 |
|   | SORBO® | Sorbitol | 11.00 |

Preparation

Procedure as in Example 1.

I claim:

1. An ethanol free clear oil-in-water transparent gel sunscreen composition comprising an oil phase comprising an oil and an emulsifier and a water phase having dissolved therein an emollient, said oil phase having dissolved therein an effective amount of ultraviolet radiation and absorbing ingredients comprising at least one p-amino-benzoic acid compound and at least one benzophenone compound.

2. A composition of claim 1 wherein said p-aminobenzoic acid compound is selected from the group consisting of octyl-p-dimethylaminobenzoate, isoamyl-p-dimethylaminobenzoate and 2-ethylhexyl-p-dimethylaminobenzoate and said benzophenone is selected from the group consisting of neutralized 2-hydroxy-4-methoxybenzophenone-5-sulfonic acid and 2-hydroxy-3-methoxybenzophenone-5-sulfonic acid.

3. A sunscreen formulation of claim 1 wherein said oil phase comprises mineral oil and an emulsifier having an HLB in the range of 1 to 19 selected from the group consisting of polyethoxylated monohydric alcohols having 14-20 carbon atoms and an ethylene oxide content of 2-25 mols per molecule.

4. A composition of claim 1 wherein said aqueous phase has dissolved therein emollients selected from the group consisting of propylene glycol and sorbitol.

5. A composition of claim 1 having 5-30% by weight of ultraviolet radiation absorbing compounds.

6. A composition of claim 1 containing 7 parts-by-weight octyl dimethyl p-amino-benzoic acid compound, 3 parts-by-weight benzophenone, 10 parts-by-weight mineral oil, 6.25 parts-by-weight oleth-2, 18.75 parts-by-weight isoceteth-20, 40 parts-by-weight water, 4 parts-by-weight propylene glycol, 11 parts-by-weight sorbitol.

* * * * *